(12) United States Patent
Armstrong et al.

(10) Patent No.: US 8,944,984 B2
(45) Date of Patent: Feb. 3, 2015

(54) RADIATION/DRUG DELIVERY METHOD AND APPARATUS

(76) Inventors: Kevin Armstrong, Irvine, CA (US); Thomas Chen, La Canada, CA (US)

( * ) Notice: Subject to any disclaimer, the term of this patent is extended or adjusted under 35 U.S.C. 154(b) by 1038 days.

(21) Appl. No.: 12/402,437

(22) Filed: Mar. 11, 2009

(65) Prior Publication Data

US 2010/0234669 A1 Sep. 16, 2010

Related U.S. Application Data

(60) Provisional application No. 61/035,665, filed on Mar. 11, 2008.

(51) Int. Cl.
*A61M 36/12* (2006.01)
*A61N 5/10* (2006.01)

(52) U.S. Cl.
CPC .............. *A61N 5/1007* (2013.01); *A61N 5/1027* (2013.01)
USPC ............................................................ 600/7

(58) Field of Classification Search
USPC .......... 600/1–8, 564–568; 606/53–86 B, 185; 604/264, 272, 278
See application file for complete search history.

(56) References Cited

U.S. PATENT DOCUMENTS

| | | | |
|---|---|---|---|
| 5,183,455 A * | 2/1993 | Hayman et al. | 600/7 |
| 5,938,582 A * | 8/1999 | Ciamacco et al. | 600/3 |
| 6,019,776 A * | 2/2000 | Preissman et al. | 606/185 |
| 2005/0131269 A1* | 6/2005 | Talmadge | 600/3 |
| 2007/0010845 A1* | 1/2007 | Gong et al. | 606/192 |
| 2007/0167664 A1* | 7/2007 | Hermann et al. | 600/3 |
| 2009/0209802 A1* | 8/2009 | Francescatti et al. | 600/3 |

* cited by examiner

*Primary Examiner* — Catherine B Kuhlman
(74) *Attorney, Agent, or Firm* — Atlantic Coast Patent Group

(57) ABSTRACT

There is provided herein a brachytherapy delivery system for the internal delivery and positioning of therapeutic agent, most particularly, a discrete radiation emitting particulate, within or in proximity to a vertebral or other bony tumor. The system comprises an elongated bone cannula having a proximal and a distal end, the distal end being suitable for disposition within bone. The bone cannula further comprises a bore disposed longitudinally therethrough suitable to axially and slidably receive an elongated and cannulated therapy delivery apparatus through which the therapeutic agent is delivered.

6 Claims, 6 Drawing Sheets

RADIATION/DRUG DELIVERY METHOD AND APPARATUS

CROSS-REFERENCE TO RELATED RELATED APPLICATION

This application claims the benefit under 35 U.S.C. §119(e) of U.S. Provisional Application Ser. No. 61/035,665, filed Mar. 11, 2008, which is hereby incorporated in its entirety by reference thereto.

BACKGROUND OF THE INVENTION

The present invention relates to methods and devices for administering radiation and/or pharmaceutical or other therapeutic agents into bony tissues, especially vertebral bone. More particularly, the present invention relates to methods and devices for treating tumors in vertebral bone.

Methodologies utilizing localized radiation and/or pharmaceuticals and chemotherapeutic agents to treat many different types of tumors are well known in the art of medicine. One particular type of such treatment commonly referred to as brachytherapy, delivers a radiation dose to soft tissue tumors by way of a discrete radiation source that is positioned in or within close proximity to the tumor site. Most conventional brachytherapy typically utilizes radioactive granules, beads, or seed particles that are embedded or otherwise deposited at the tumor site through a series of cannulated needles or other brachytherapy apparatus. These techniques are useful in that, in contrast to external radiation therapies where the radiation dose is delivered through a beam that must often pass through healthy tissues, brachytherapy affords a more direct delivery of the radiation dose to the cancerous cells while minimizing undesirable radiation exposure to healthy cells.

Importantly, it will also be understood and appreciated by those skilled in the art that such brachytherapy systems may also be utilized to treat non-cancerous pathologies such as viral or bacterial infections and the like. Accordingly, these systems may be similarly adapted and utilized for the delivery of other therapeutic agents such as, but not limited to, chemotherapeutic compounds, gene therapy formulations, antibacterials, anti-fungals, etc.

Radiation therapy regimens are typically dependent upon the size and type of the tumor and it is often desirable to serially administer the therapy at different times within a day or over several days. In most conventional brachytherapy systems, which are primarily engineered for treating soft tissue tumors, the clinician typically guides either a brachytherapy needle assembly, catheter, or some other brachytherapy delivery apparatus into the tumor. The radiation source is subsequently delivered therethrough and the tumor is exposed to the desired dose of radiation. The delivery apparatus is then removed or electively left in place for subsequent treatment sessions. Optionally, the radiation source may be removed once the exposure time has elapsed.

One early brachytherapy technique, as disclosed in U.S. Pat. No. 4,402,308 to Scott, involves the use of sheathed needle injector for depositing radioactive "seeds" in a tumor. The injector comprises a hollow, needle sheath with a sharpened point suitable for injecting into human tissue and a slotted needle slidably and rotatably mounted inside the sheath. The sheath is retractable to expose the entire needle or any desired portion thereof.

The Scott patent, hereby incorporated herein by reference thereto, points out that it has been a common technique in the treatment of malignant tumors to inject radioactive seeds into a tumor to provide radiation therapy. These seeds are typically small discrete units filled with a radioactive material and sealed at each end. They may be of any convenient size although they are most often less than one millimeter in diameter and 3-4 millimeters in length. The number and positioning of the seeds in the tissue depends upon the treatment considered most appropriate by the physician.

Scott further points out that devices for accomplishing these implantation treatments have varied considerably. One of the first of such treatments is disclosed in U.S. Pat. No. 2,269,963 wherein a device having an appearance similar to that of a handgun, is utilized to deposit radioactive seeds by deploying a plunger into the barrel of the device. Techniques involving such guns or needles to implant seeds have proved to be deficient in many respects, primarily because they do not provide a means for implanting seeds at a precise spacing and location to perform the desired treatment. Accordingly, it is will be readily understood and appreciated by those skilled in the art that the more accurately a clinician can position and maintain a radiation source in a tumor, the more effective the sphere of radiation exposure will be.

Such deficiencies led Scott and others to seek alternative devices and methods by which radioactive seeds could be positioned in a fixed spaced relationship to each other, one method being the use of a suture containing the seeds in a predetermined array. After the suture was threaded into the tissue, the suture material would be absorbed by the body leaving the seeds positioned in a fixed spaced relationship. Such a suture approach had limited applicability in deep tissues so the same basic idea was employed using a needle to inject seeds separated by absorbable spacers.

Scott developed a sheathed needle injection device that was loaded with seeds but without any absorbable spacers. The sheathed needle device was intended for insertion into the tissue of interest whereupon the seeds were expelled from the needle through slots in the sheath. The entire sheathed needle device was subsequently withdrawn from the patient leaving the seeds deposited in the tissue. According to Scott, this device was a vast improvement over previous techniques yet it lacked some precision in positioning the seeds because the method of ejecting seeds from the needle functioned imperfectly. Subsequently, Scott developed a new and improved injector for implanting radioactive seeds in human tissue with precision as disclosed in the '308 patent.

Some shortcomings associated with the aforementioned devices and techniques are highlighted by U.S. Pat. No. 7,497,818 to Terwilliger, which is hereby incorporated herein by reference thereto. Terwilliger points out that despite any differences in the foregoing approaches, such techniques typically result in the radioactive seeds being deposited in the track made by the needle. As the needle is withdrawn, there is a tendency for the seeds to migrate in the needle track resulting in a poor distribution of the seeds and compromising the intended sphere of radiation. Terwilliger further points out that these seeds often continue to migrate over time resulting in the need for additional implant sessions that are costly and uncomfortable for the patient.

Terwilliger further notes that to address the foregoing problems, other prior art was developed to introduce seeds into the tumor site using a bioabsorbable, pre-manufactured, elongated assembly or implant that was capable of being loaded into an "introducer needle" prior to the procedure. Unfortunately, such implants have many drawbacks including positioning problems as well as the inability of the implant to flex with the tissue over the time necessary for the bio-absorbable material to dissolve. Moreover, as the tissue or gland recedes or shrinks back to pre-operative size, these implants often tend to remain stationary and do not move with the tissue. Accordingly, the final location relative to the tumor site is not maintained and the dosage of the radioactive seeds does not meet the preoperative therapy plan.

Terwilliger further cites U.S. Pat. No. 6,163,947 to Coniglione, also incorporated herein by reference thereto, wherein there is disclosed a string of hollow seeds as described in U.S. Pat. No. 5,713,828 that are strung onto a thin strand of suture material to form an array of seeds. This string of seeds is delivered into the tumor site placed within a hollow delivery needle. The difference in diameter between the seed and the thin suture material makes the assembly susceptible to collapse from axial force applied on the proximal end, thereby resulting in the assembly typically becoming jammed within the needle lumen and/or the assembly not maintaining the proper desired spacing between radioactive seeds as it is positioned into the treatment site.

To address the foregoing problems and to provide an alternative to the cited prior art, Terwilliger discloses a delivery system comprising a bioabsorbable, elongated implant having a plurality of radioactive seeds pre-dispersed therein in a prearranged orientation. The elongated implant member has sufficient axial rigidity in order to allow expulsion of the member while maintaining the spacing between seeds. The member is designed with enough flexibility/pliability to move in conjunction with the surrounding tissue as it shrinks back to a pre-operative size. According to Terwilliger, the seeds maintain their spacing, even after being introduced into the body, and this affords accurate placement and retention of the seeds in accordance with the physician's preoperative treatment plan.

Various implant alternatives to Terwilliger other than those cited above are also well known in the prior art. For example, U.S. Pat. No. 7,322,928 to Reed, which is also incorporated herein by reference thereto, discloses an absorbable suture member having radioactive seeds and spacer members predeterminantly disposed therein which is delivered through a conventional brachytherapy needle or the like. Other such implants include those disclosed in U.S. Pat. Nos. 7,329,259, 7,244,226, 6,264,600, 4,815,449, and 4,697,575, all of which are hereby incorporated herein by reference thereto.

As will be appreciated by those skilled in the art from a reading of the foregoing references, most of the conventional prior art brachytherapy devices and techniques utilize permanent or semi-permanent implantation of a radioactivity source at the tumor site often in a single treatment session. While the permanence of such implantation may be somewhat limited due to the radioactive half-life of the isotopes employed as well as the biodegradable nature of the containment housings or other vehicles implanted along with such isotopes, the permanence or semi-permanence is clearly a prior art shortcoming based upon the increased exposure of the patient to the resulting radioactivity over an extended period of time.

Additionally, the patient becomes an environmental source of radioactivity and must therefore avoid contact with certain people such as pregnant women and young children. Moreover, because the radioactivity remains in the patient for an extended period of time rather than affording a discrete and controlled exposure time, the use of higher radiation dosages and certain radioisotopes are often precluded for this type of technique. This, of course, limits the physician's flexibility in treatment regimens as well as the implementation of more aggressive radiation treatment strategies.

In addition to the brachytherapy implants referenced above, a variety of soft tissue brachytherapy techniques involving needle assemblies are also known in the prior art. Typically these techniques involve loading radioactive seeds into a series of needles that are then inserted into the treatment site, such as the prostate, utilizing ultrasound imaging to guide the insertion process. The radioactive seeds are positioned either independently within the needles or with spacers and expelled accordingly.

These needle assemblies can be fabricated in a variety of configurations such as, for example, those disclosed in U.S. Pat. Nos. 7,131,942 and 7,282,020, to Taylor and Kaplan, respectively, both of which are hereby incorporated herein by reference thereto. In particular, the '942 patent to Taylor discloses a brachytherapy needle assembly wherein a tubular sleeve containing discrete radioactive seeds is slidably and axially received within a needle that is, in turn, slidably positioned within an outer sleeve, the entire assembly being inserted into a soft tissue tumor to expel the radioactive seeds at the desired location. A stylet or obturator is driven through the tubular sleeve to deposit the seeds.

The '020 patent to Kaplan discloses a similar configuration wherein a stylet or obturator is slidably and axially received in a cannulated needle that, in turn, is slidably received in an outer sleeve. Radioactive seeds are positioned within the needle and the entire device is inserted into the patient. Once the device is in position, the stylet or obturator can be advanced to dispel the seeds in the desired location. In an alternative embodiment, the needle is replaced with a trocar that is similarly loaded with radioactive seeds. Other such needle assemblies include those disclosed in U.S. Pat. Nos. 7,361,135, 7,247,160, 7,104,945, 5,938,583, 5,928,130, 5,860,909, 4,815,449, and 4,697,575, all of which are hereby incorporated herein by reference thereto.

It will be understood and appreciated by those skilled in the art that all of the foregoing brachytherapy techniques and devices are primarily engineered for the treatment of soft tissue tumors. Spinal tumors as well as other tumors of the bone unfortunately create a unique challenge for these conventional brachytherapy techniques as the density of bone is significantly greater than that of soft tissues. Moreover, vertebral tumors have the added complication of proximity to highly sensitive neural and vascular anatomy further rendering conventional soft tissue brachytherapy apparatus and techniques unacceptable.

In particular, many of these soft tissue brachytherapy techniques require multiple needle insertions per treatment session to achieve an adequate sphere of radiation exposure at the tumor site. In the treatment of a vertebral tumor, this would result in increased risk to the patient's neural and vascular anatomy as well as additional complexities for the clinician who must forcibly insert multiple brachytherapy needle assemblies into vertebral bone. These shortcomings are even further complicated in the event that the patient's treatment regimen requires repeated, serial radiation exposures over several treatment sessions which may typically span over a few days or weeks. Such sessions are expensive and uncomfortable for the patient.

Additionally, similar to the radiation exposure problems observed in the implant technologies previously mentioned, these needle assemblies are typically designed to deliver discrete radiation particles that remain in the patient until the half-life of the radioisotope exhausts itself. Accordingly, the exposure considerations set forth above are not avoided by these brachytherapy alternatives. Moreover, unlike the implant technologies, these prior art needle assemblies do not address the problem of "seed migration" as discussed above.

U.S. Pat. Nos. 7,381,178 and 7,494,457 to Winkler, both of which are hereby incorporated herein by reference thereto, disclose various embodiments of a brachytherapy device for treating tumors in vertebral bone. The device includes a catheter member and a structural support member cooperatively attached thereto, the structural support member being designed to fit in an interstitial space that has been created by the surgical resection of the vertebral tumor. In particular, the device is designed to irradiate any cancerous remnants of the tumor that may appear in the margins of the excision. In one embodiment of the invention, a balloon catheter designed to be an inflated within the structural support member is used to deliver the radiation source.

One noteworthy shortcoming of the Winkler devices results from the dependency of the device's effectiveness on the previous excision of the tumor in conjunction with the placement of the support member within the interstitial space created by the excision. Such a treatment approach is clearly limited to situations conducive to such surgical intervention as well as anatomic constraints that may severely limit or prohibit the placement of the support member.

In light of the shortcomings of the foregoing prior art, it would be clearly advantageous for the clinician to have an alternative delivery method to apply radiation therapy or other therapeutic agents directly at bone tumor site within a vertebral body or other bony structure with a minimum amount of invasiveness and discomfort to the patient, especially where subsequent treatments sessions are desired.

Moreover, it would be similarly advantageous to deliver brachytherapy to a bone tumor without the problems of "seed migration" and extended exposure times that may compromise or prohibit the use of certain radioisotopes as well as high dosing regimens.

SUMMARY OF THE INVENTION

The present invention is directed to a brachytherapy delivery system for the internal delivery and positioning of a therapeutic agent within bone. The system comprises an elongated and continuous bone sheath/bone cannula having an open proximal end an optionally open distal end, the bone cannula having an axial bore running longitudinally therebetween.

In order for the bone cannula to perform as contemplated by the present invention, at least the distal fourth of the cannula should be preferably constructed of a medical grade material sufficient to impart adequate rigidity and resiliency for insertion and retention in bone. It is preferably this segment of the bone cannula that will be ultimately embedded in bone despite any modifications contemplated in the various embodiments of the device or procedures of the present invention.

The system also includes an elongated, therapy delivery apparatus that has a proximal and a distal end with an axial bore running longitudinally therebetween for the passage and deposition of the therapeutic agent. In accordance with the present invention, the therapy delivery apparatus is to be axially and slidably received into the bone cannula. As such, it will be understood and appreciated by those skilled in the art of biomedical engineering that the therapy delivery apparatus should clearly be of a suitable diameter and length to be slidably received within the bone cannula in order to deliver the therapeutic agent to a desired site in the bone.

It will further be appreciated that the brachytherapy delivery system of the present invention, while predominantly engineered for the delivery of a radiologic therapeutic, may be similarly adapted and utilized for the delivery of a variety of non-radiologic therapeutic agents and, moreover, may be analogously utilized to treat various non-cancerous pathologies such as viral or bacterial infections and the like. Some non-limiting examples of such non-radiologic therapeutic agents include chemotherapeutic compounds, gene therapy formulations, antibacterials, anti-fungals, etc. which may, in turn, also be effectively delivered to treat a variety of pathologies through the use of the present invention.

Those skilled in the art of radiation oncology will appreciate that a variety of brachytherapy agents may be deployed to the tumor site using the system of the present invention. These agents may be in liquid, or are plasma, or particulate form and may often be compartmentalized in discrete seeds, beads or granules well known in the art.

Also disclosed is a method of treating a patient by serially delivering a therapeutic agent such as a radioactivity source or a chemotherapeutic agent to the site of a bone pathology such as a tumor, an infection, or other pathology or lesion present in bone. The method of treatment will typically span multiple treatment sessions and begins with the positioning of the bone cannula of the present invention within the patient by the use of fluoroscopy techniques, surgery, or other suitable means known in the art one of which is further described hereinbelow.

The bone cannula can, in one embodiment for example, be inserted into the patient in conjunction with a trocar or other similar sharp-tipped instrument that has been slidably received through the entire length of the cannula, thereby exposing the sharpened tip. In this manner, the distal end of the bone cannula can be driven into and received directly into the bone at the site of the lesion while the proximal end of the cannula remains accessible to the clinician in order to receive a cooperating apparatus that is used to deliver the therapeutic agent. In another embodiment of the invention the clinician can fashion a channel into the tissue using any of various operative techniques known in the art.

Once the bone cannula has been properly positioned in the desired orientation, a therapy delivery apparatus is inserted into the proximal end of the cannula and advanced to the desired depth for the effective delivery of the therapeutic agent directly into the site of the bone lesion. After the therapy delivery apparatus has been positioned, a therapeutic agent is delivered. Following the completion of such delivery, the clinician may optionally remove the therapeutic agent from the patient after a predetermined exposure time has elapsed. The therapy delivery apparatus is then preferably removed from the bone cannula, which can remain positioned in the patient for subsequent treatment sessions.

The clinician may then optionally obstruct the bone cannula in order to protect its bore/lumen from infiltration by foreign objects and/or internal bodily fluids or other undesirable infiltrates. In order to properly obstruct the cannula, the clinician will typically employ a trocar or other insertable instrument such as an obturator or stylet that can remain in the bore of the bone cannula until a subsequent treatment session is initiated. In such a situation, the proximal end of the cannula will preferably remain sub-cutaneously accessible to the clinician through operative fluoroscopy techniques or other means even though the outer dermis will undergo the appropriate wound closure protocol to prevent infection.

In the event that a subsequent treatment session is desired, the clinician may then remove any such instrument that may have been inserted into the bone cannula to temporarily block the same followed by the reinsertion of the therapy delivery apparatus into the bone cannula in order to initiate the delivery of another intended dose of the therapeutic agent. While the delivery system of the present invention is primarily intended for use with serial therapy regimens, it is clearly contemplated herein that the system could be used for single dosing event as well.

Accordingly, the present invention advantageously provides for a new and improved delivery method and system for applying radiation therapy or depositing other therapeutic agents directly at a bone tumor site within a vertebral body or other bony structure.

Moreover, the present invention also advantageously provides for a brachytherapy kit that comprises the aforementioned bone cannula and the therapy delivery apparatus as well as a therapeutic agent to be used therewith.

In further contrast to the prior art brachytherapy methods and devices set forth above, the features of the present invention facilitate multiple treatment sessions with minimal invasiveness to the patient who would otherwise have to endure repeated surgical placement of catheters or mutiple needles to attain effective delivery of a brachytherapy radiation source or other therapeutic agents.

As will be appreciated by those skilled in the art, the device and method of the present invention also allows for the removal of the therapeutic agent between treatment sessions with minimal discomfort to the patient. Such an advantage further provides the physician with various options by which he can optimize the radiation therapy regimen on an individualized basis. In particular, since the bone cannula is designed to remain in place between treatment sessions and affords the optional removal of the radiation dose after the intended exposure time, the physician gains added flexibility in the treatment regimen to dose the patient more frequently with a higher radiation dose over shorter intervals. Because the nature and stage of the tumor often affects the physician's choice of treatment plans, the present invention advantageously affords clinical flexibility while preserving the conventional brachytherapy advantages such as localized radiation delivery with minimal exposure of healthy tissue.

Accordingly, other advantages and features of the present invention will be apparent to those of ordinary skill in the art in view of the following detailed description of the various embodiments of the invention and accompanying drawings.

BRIEF DESCRIPTION OF THE DRAWINGS

The drawings as provided for herein set forth exemplary embodiments of the present invention, the detailed description of which follows hereinbelow. The drawings are merely exemplary and are clearly not intended to limit the invention as encompassed by the claims appended herewith.

DETAILED DESCRIPTION OF THE INVENTION

Figure 1:
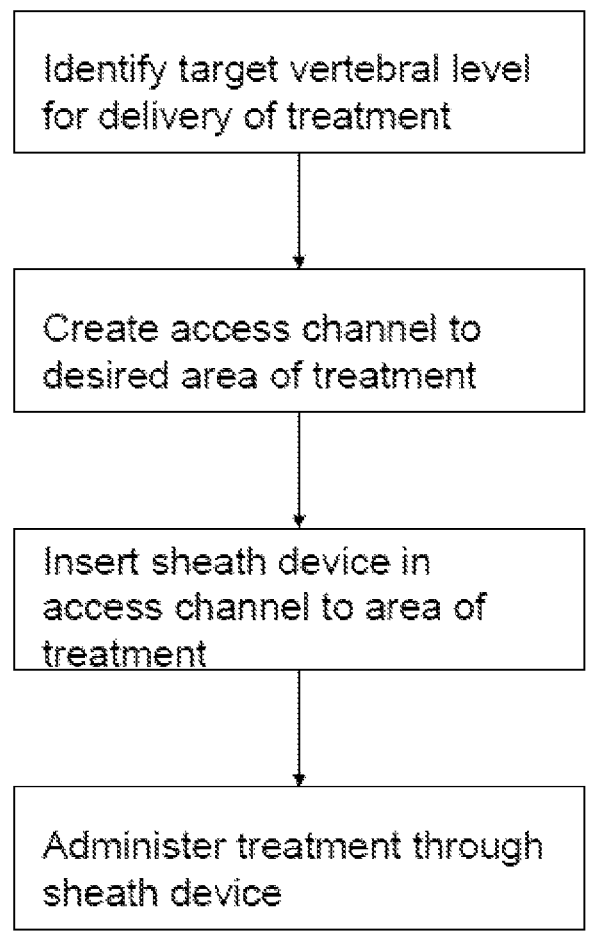
FIG. 1 is a flowchart illustrating the basic steps in utilizing the delivery system of the present invention.
Figure 2:
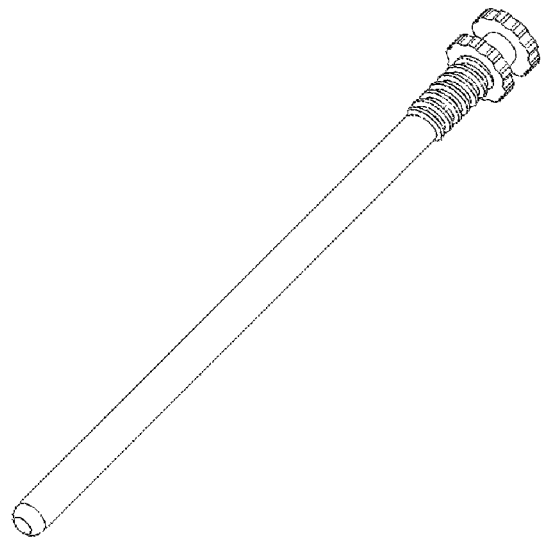
FIG. 2 is an enlarged perspective view of one embodiment of a threaded obturator designed to be inserted and threadably coupled to the bone cannula of the present invention.
Figure 3:
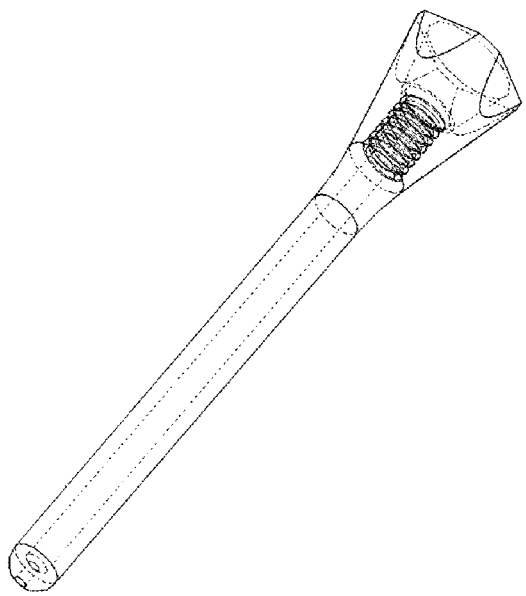
FIG. 3 is an enlarged perspective view of one embodiment of the bone cannula of the present invention.

The following description is made in general reference to FIGS. 1-12 that are provided herewith solely to illustrate exemplary embodiments of the present invention.

In accordance the present invention, there is described herein a brachytherapy delivery system for the internal delivery and positioning of a therapeutic agent within bone. It will further be appreciated that the brachytherapy delivery system of the present invention, while predominantly engineered for the delivery of a radiologic therapeutic, may be similarly adapted and utilized for the delivery of a variety of non-radiologic therapeutic agents and, moreover, may be analogously utilized to treat various non-cancerous pathologies such as viral or bacterial infections and the like. Some non-limiting examples of such non-radiologic therapeutic agents include chemotherapeutic compounds, gene therapy formulations, antibacterials, anti-fungals, etc. which may, in turn, also be effectively delivered to treat a variety of pathologies through the use of the present invention.

The system includes an elongated and continuous bone cannula having an open proximal end and an optionally open distal end, the bone cannula having an axial bore running longitudinally therebetween (see for example, FIGS. 3, 8, 9, and 10). In order for the bone cannula to perform as contemplated by the present invention, at least the distal fourth of the cannula should be preferably constructed of a medical grade material sufficient to impart adequate rigidity and resiliency for insertion and retention in bone. It is preferably this segment of the cannula that will be ultimately embedded in bone despite any modifications contemplated in the various embodiments of the device or procedures of the present invention.

While it is preferable to form the entire bone cannula of the present invention out of a single type of continuous material such as a suitable medical grade polymer, co-polymer or metal such as stainless steel or titanium, it will be appreciated that the distal fourth of the cannula may be fashioned from a material different than the remaining portion, although this may prove considerably more expensive. As such, the entire bone cannula will be preferably made from a suitable medical grade polymer or co-polymer or other suitable material such as any of several medical grade metals or alloys known in the art, some non-limiting examples being stainless steel or titanium.

It will be appreciated that various suitable polymeric materials are well known and readily available to the art of medical design engineering and include but are not limited to thermosetting polymers, thermoplastic polymers, and mixtures thereof. Moreover, it will be further apparent to those skilled in the art that selection of such polymers or copolymers should be such that the resulting polymeric matrix formed thereby is capable of withstanding the insertion and retention forces mentioned above when the device is driven into bone.

In a further embodiment, the polymer or copolymer is comprised of at a least one of the polymeric materials selected from the following group: poly-ether-ether-ketone (PEEK), poly-ether-ketone-ketone (PEKK), poly-methylmethacrylate (PMMA), polysulfone, polylactide (PLA), poly-L-lactide (PLLA), and poly(glycolic acid) (PGA). Those skilled in the art will appreciate that some instances a ketone-based polymer such as poly-ether-ether-ketone (PEEK) or poly-ether-ketone-ketone (PEKK) would be preferred.

The length of the device will vary depending upon the application. Typical lengths will be between 30 and 60 mm while the diameter of the longitudinal bore will vary between 3 to 8 mm. As previously noted, the proximal end will be open and the longitudinal bore will be suitable for receiving a catheter or other therapy delivery apparatus through which the radiation source or other therapeutic agent is passed (see for example, FIGS. 3, 8, and 9).

In the event that the bone cannula is contemplated to be inserted into bone using a trocar or other suitable cannulating instrument, the distal end of the cannula should be fashioned with an open configuration so as to allow the sharpened distal tip of the trocar or similar instrument to protrude therefrom so that it can cannulate the bone during the insertion process. As will be discussed below, the present invention contemplates, for example, that a trocar may also be used as a very simplistic version of the therapy delivery apparatus of the present system.

An additional feature of the aforementioned embodiment contemplates that the distal opening of the bone cannula also serve to facilitate insertion and proper positioning of the cannula over a guide wire or other guidance means. It will be appreciated by those skilled in the art that in the event that the distal end of the bone cannula is closed ended and/or blunted, an insertion channel must be fashioned into the patient by the clinician prior to the insertion of the cannula.

Moreover, it will be further appreciated that in some circumstances it will be intended that distal end of the cannula have no aperture, as might be the case when the system is to be utilized with a radiation source that is contemplated to be removed from the patient once a predetermined exposure time has elapsed. Importantly, in those cases where it is contemplated to remove the radiation source after such time, it is not mandatory that the distal end of the cannula be closed, however. Those skilled in the art can readily visualize how a balloon catheter, for example, or other therapy delivery apparatus having a distal radiation source containment feature might be passed through a distal opening or aperture in the bone cannula of the present invention and subsequently inflated, at least to a degree, in order to position a radiation source at the desired location for a predetermined exposure time and then removed.

It can also be further appreciated that certain embodiments of the bone cannula can potentially include a sequence of interconnecting or telescoping-type tubes made of any appropriate medical grade material acceptable in the art. Suitable materials would include but are not limited to medical grade polymers such as PEEK and appropriate medical grade metals as mentioned above. Such tubes could be optionally manufactured with a bore that may or may not extend all the way through the tube as discussed above. Importantly, it should be noted that the bone cannula of the present invention may be inserted into the vertebral body via the pedicle or directly into the vertebral body and should have sufficient length so as to remain, at a minimum, sub-cutaneously accessible to the clinician by fluoroscopy techniques when fully inserted into the vertebral body in order to facilitate the delivery of the therapeutic agent to the affected area.

Optionally, the proximal end of the bone cannula can include threading on the internal surface of the bore just distal to the opening in order to threadably receive a reciprocally threaded obturator, stylet, plunger or trocar as described in more detail hereinbelow. Moreover, just proximal to the internal threading, the bone cannula may be preferably funneled or beveled to facilitate the introduction of an obturator, stylet, plunger, trocar, catheter or other therapy delivery apparatus into the bore.

Figure 4:
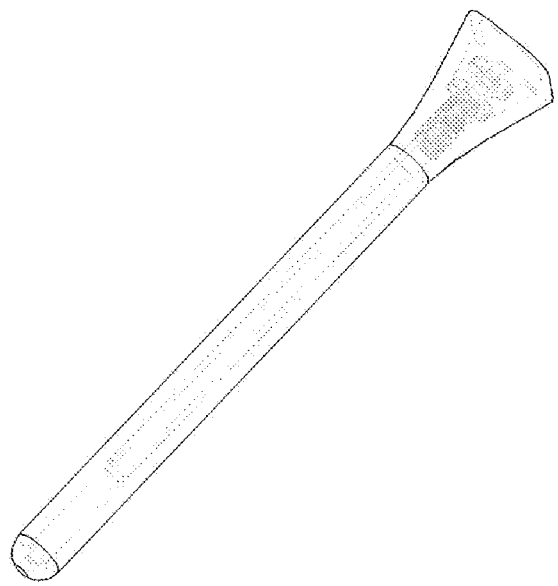
FIG. 4 is an enlarged perspective view of the threaded obturator of FIG. 2 inserted and threadably coupled to the bone cannula of FIG. 3.
Figure 5:
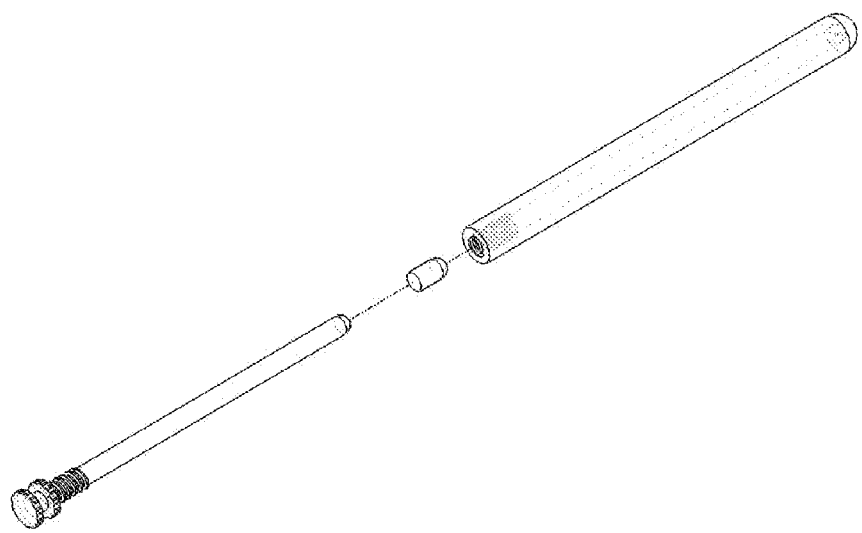
FIG. 5 is an exploded view of the obturator of FIG. 2 prior to insertion into the bone cannula of FIG. 3 in conjunction with a radiation seed pellet.
Figure 6:
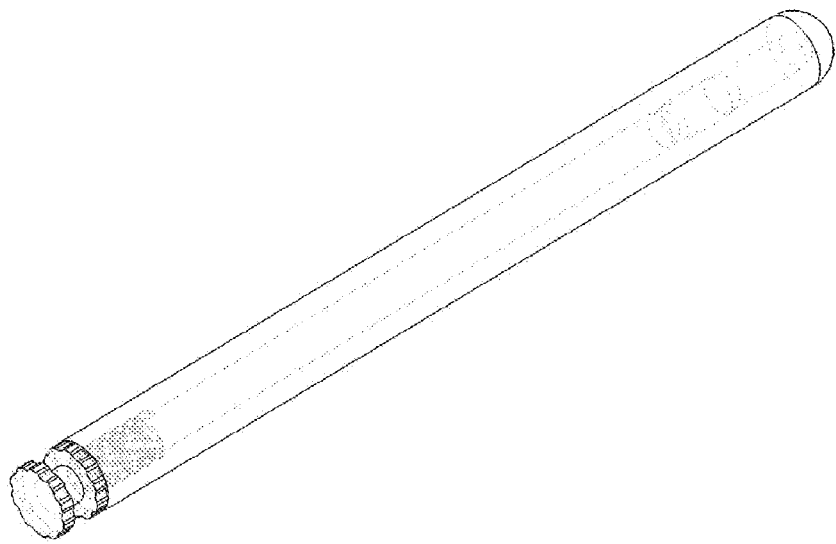
FIG. 6 is an enlarged perspective view of the threaded obturator of FIG. 2 inserted and threadably coupled to the bone cannula of FIG. 3 in conjunction with a radiation seed pellet.
Figure 7:
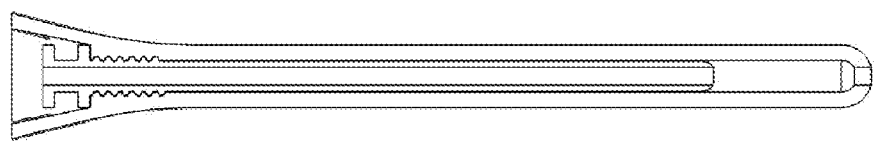
FIG. 7 is an enlarged side view of the threaded obturator of FIG. 2 inserted and threadably coupled to the bone cannula of FIG. 3.
Figure 8:
FIG. 8 is an enlarged side view of the bone cannula of FIG. 3.
Figure 9:
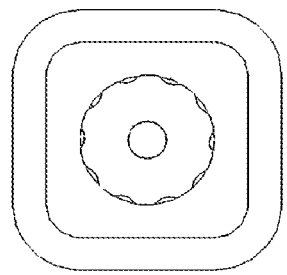
FIG. 9 is an enlarged frontal view of the flared proximal end of the bone cannula of FIG. 3.
Figure 10:
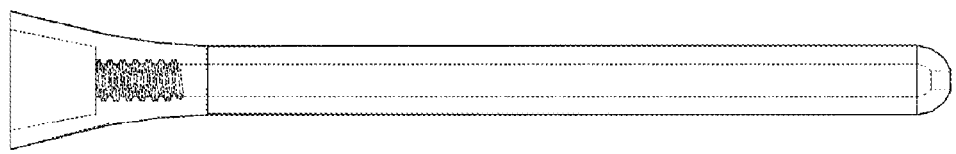
FIG. 10 is an additional enlarged side view of the bone cannula of FIG. 3.
Figure 11:
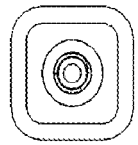
FIG. 11 is an enlarged frontal view of the flared proximal end of the bone cannula as seen in FIG. 4 having the obturator of FIG. 2 inserted and threadably coupled therein.
Figure 12:
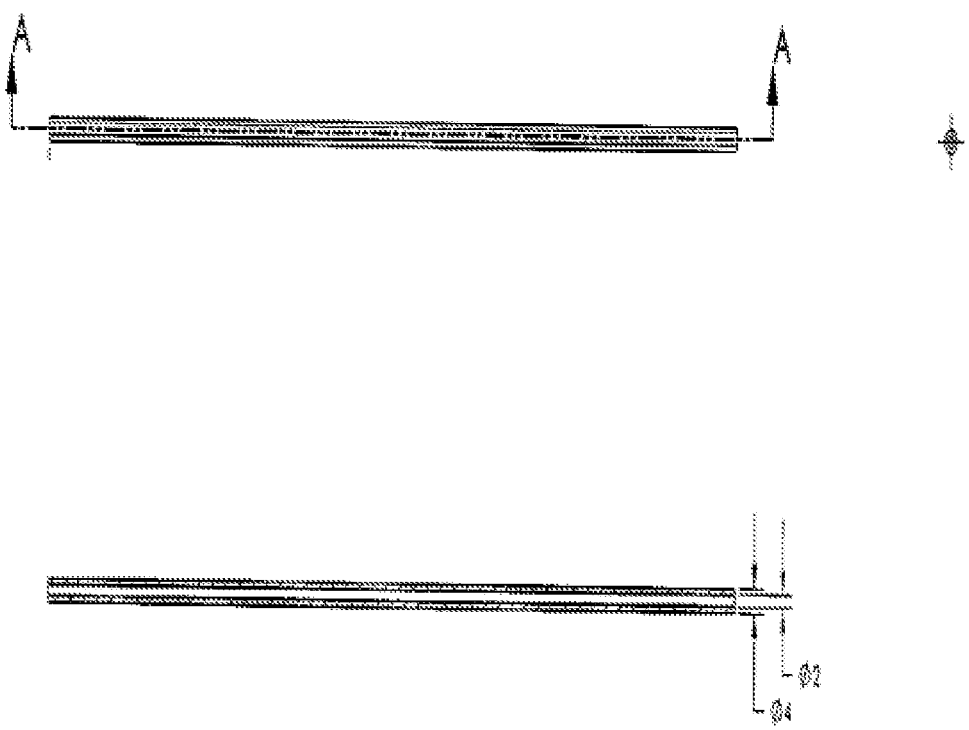
FIG. 12 is a sectional view across line A-A of the lumen section of the bone of the present invention.

In one further preferred embodiment, an obturator, stylet, plunger or trocar may be fashioned with a reciprocally cooperative threading so that when it is placed into the bore of the bone cannula it may be securely fastened therein (see for example, FIGS. 4, 6, and 7). Accordingly, it may be further preferred to provide some extension member or handle on the proximal end of the aforementioned instruments in order to facilitate the rotational movement required to threadingly secure such instrument into the bone cannula. It will be appreciated that this feature of the present invention advantageously affords the clinician the option to intentionally obstruct the bone cannula in order to protect its bore/lumen from infiltration by foreign objects and/or internal bodily fluids or other undesirable infiltrates.

The system of the present invention also includes an elongated, therapy delivery apparatus that can take on a variety of configurations known in the art so long as such configuration has a proximal and a distal end with an axial bore running longitudinally therebetween for the passage and deposition of a therapeutic agent and conforms to the additional parameters set forth below. As will be readily appreciated by those skilled in the art, the proximal end of such apparatus is typically open-ended or includes an otherwise accessible portal or aperture by which the clinician can introduce a therapeutic agent, the most common example of which is a catheter or micro-laparoscopic delivery device.

As will be further appreciated, the proximal end of the apparatus most often remains on the external aspect of the patient so that it can be manipulated by the clinician as needed. The distal end of such apparatus is, of course, designed and suitable for insertion into and retention within the cooperating bone cannula of the present invention. Clearly it will be appreciated that the length of the apparatus must be adequate enough for the distal end to be received in the distal end of the sheath/bone cannula or, alternatively, a few millimeters therebeyond in order to access the bone pathology targeted for treatment.

Other more simplistic yet suitably effective configurations for the therapy delivery apparatus of the present invention include trocars and other cannulated instruments, all of which are well known in the art for the cannulated delivery of a therapeutic agent.

It will be additionally appreciated that the therapy delivery apparatus of the present invention must be of suitable dimensions and clinically effective tolerances to be axially and slidably received into the bone cannula in a manner that safely and effectively delivers the therapeutic agent to a desired site in the bone.

In accordance with the present invention, one exemplary embodiment of the aforementioned delivery apparatus is a catheter that is advanced through the bore of the bone cannula. More particularly, such a catheter may for example be a "balloon tied catheter". These catheters typically have a balloon suitably positioned at a point on the catheter to effectively create an inflatable compression force that is adequate to secure the catheter within the cannula. Such a feature advantageously prevents any repositioning of the catheter, and consequently the therapeutic agent. It will be appreciated that any movement of the catheter during a brachytherapy session will likely compromise the effectiveness of the treatment as such movement may unfavorably alter the intended sphere of radiation set forth in the clinician's treatment plan.

It will be readily apparent to those skilled in the art that an acceptable therapy delivery apparatus can be readily fashioned from any one of many prior art devices well known in the art, several of which are disclosed, for example, in U.S. Pat. Nos. 7,476,235, 6,746,392, 6,673,006 6,482,142, 6,413,204, and 5,916,143, all of which are hereby incorporated herein by reference thereto.

It will be further understood and appreciated by those skilled in the art of radiation oncology that a variety of brachytherapy agents may be deployed at the tumor site using the system of the present invention. These agents may be in liquid, plasma, or particulate form and may often be compartmentalized as a discrete radiation emitting particulate such as but not limited to seeds, beads, or granules that are well known in the art.

By way of a further non-limiting example, seeds of various types are available and well known in the art, multiple examples of which are cited in Terwilliger '818 as referenced above. Some non-limiting examples of radioactive isotopes include iridium 192, cesium 131, gold 198, yttrium 90 and phosphorous 32. Seeds such as those described in U.S. Pat. 6,248,057, which is incorporated herein by reference thereto, can similarly be used with the system and methods contemplated by the present invention.

In accordance with another aspect of the present invention, there is also provided a method for treating a patient by serially delivering a therapeutic agent such as a radioactivity source or a chemotherapeutic agent to the site of a bone pathology such as a tumor, an infection, or other pathology or lesion present in bone. The method of treatment will typically span multiple treatment sessions and begins with the positioning of the bone cannula of the present invention within the patient by the use of fluoroscopy techniques, surgery, or other suitable means known in the art, one of which is further described hereinbelow in the examples.

The bone cannula can, for example, be inserted into the patient in conjunction with a trocar or other similar sharp-tipped instrument that has been slidably received through the entire length of the cannula thereby exposing the sharpened tip. In this manner, the distal end of the bone cannula can be driven into and received directly into the bone at the site of the lesion while the proximal end of the cannula remains accessible to the clinician in order to receive a cooperating apparatus that is used to deliver the therapeutic agent. In another embodiment of the invention the clinician can fashion a channel into the tissue using any of various operative techniques known in the art.

Once the bone cannula has been properly positioned in the desired orientation, a therapy delivery apparatus is inserted into the proximal end of the cannula and advanced to the desired depth for the effective delivery of the therapeutic agent directly into the site of the bone lesion. After the therapy delivery apparatus has been positioned, a therapeutic agent is delivered. Following the completion of such delivery, the clinician may optionally remove the therapeutic agent from the patient after a predetermined exposure time has elapsed. The therapy delivery apparatus is then preferably removed from the bone cannula, which can remain positioned in the patient for subsequent treatment sessions.

The clinician may then optionally obstruct the bone cannula in order to protect its bore/lumen from infiltration by foreign objects and/or internal bodily fluids or other undesirable infiltrates. In order to properly obstruct the cannula, the clinician will typically employ a trocar or other insertable instrument such as an obturator or stylet that can remain in the bore of the bone cannula until a subsequent treatment session is initiated. In such a situation, the proximal end of the cannula will preferably remain sub-cutaneously accessible to the clinician through operative fluoroscopy techniques or other means even though the outer dermis will undergo the appropriate wound closure protocol to prevent infection.

In the event that a subsequent treatment session is desired, the clinician may then remove any such instrument that may have been inserted into the bone cannula to temporarily block the same followed by the reinsertion of the therapy delivery apparatus into the bone cannula by fluoroscopy or other means in order to initiate the delivery of a subsequent dose of the therapeutic agent. While the delivery system of the present invention is primarily intended for use with serial therapy regimens, it is clearly contemplated herein that the system could be used for single dosing event as well.

EXAMPLE 1

The invented method will first entail locating the insertion point to the desired area of treatment. Placing the patient in an appropriate position, the clinician can use a C-arm to identify the appropriate vertebral body or bony tumor location in the desired entry point into the pedicle, vertebral body or bone.

Next, a physical channel to the tumor treatment area needs to be created. There are many methodologies known in the art for creating such a channel. Each method has its respective advantages. Accordingly, it will be apparent to the physician that the choice of such methods will depend upon the nature and path of the channel to be created.

For example, utilizing a cannulated or non-cannulated jam sheedy or other appropriate instrument, the clinician can advance the instrument into the vertebral body placing its tip in the desired location relative to the tumor. In the event a cannulated needle is used, the trocar will be removed from the needle. In another exemplary embodiment, a k-wire can be placed through the cannula in the needle and the needle removed leaving the k-wire in place. If deemed appropriate, tissue dilators can be placed over the k-wire to create a working channel down the top of the pedicle. To expand the hole to accept a bone cannula and/or radiation source and taking care not to advance the k-wire, a cannulated drill or pedicle finder corresponding to the diameter of the bone cannula can be advanced down over the k-wire and into the vertebral body or bone to a depth deemed appropriate for the location of the tumor.

EXAMPLE 2

After the hole has been expanded, if the bone cannula has the aforementioned opening in the end or the long tube style is used, the cannula can be delivered over the k-wire or a drill or pedicle finder and the k-wire will be removed and the bone cannula can be advanced into the cavity that has been created. A balloon catheter can then be advanced into the bore in the bone cannula and the therapeutic entity can be delivered to the desired tumor location in the appropriate dosage. In the event that serial therapy should be desired prior to removal of the cannula, appropriate wound care management should be provided during the period that the bone cannula remains in the patient. In the event that serial therapy should occur over a several day period, a catheter may be removed and replaced with a trocar that is positioned within the bone cannula followed by appropriate wound closure techniques. Upon the next desired treatment session, a k-wire may be used to re-introduce the dilator and replace the catheter for subsequent treatments.

The foregoing is description and selected examples are provided for purposes of illustrating, explaining, and describing various exemplary embodiments of the present invention. Modifications and adaptations to these embodiments will be apparent to those skilled in the art and may be readily made without departing from the scope or spirit of this invention, certain of which is set forth below in the appended claims.

What is claimed is:

1. A method of serially delivering a therapeutic agent to a site of a bone pathology in a patient by way of multiple treatment sessions wherein the outer dermis undergoes wound closure, the method comprising:
   a) positioning within such patient a bone cannula having a proximal and a distal end, the cannula having an internal aspect including cannular threading disposed on the internal aspect of the proximal end of the cannula suitable for creating a cooperative threadable coupling with a reciprocally threaded operative instrument or apparatus at the proximal end whereby the distal end of the bone cannula is received directly into the site of the bone pathology while the proximal end remains accessible for a subsequent treatment session and is subcutaneously positioned to render wound closure;
   b) inserting a therapy delivery apparatus having a proximal end comprising threading that is cooperatively receivable by the cannular threading on the internal aspect of the cannula into the proximal end of the bone cannula and feeding the apparatus into the cannula to a depth adequate for delivering an intended dose of the therapeutic agent directly to the site of the bone pathology;
   c) delivering the intended dose of the therapeutic agent to the site of the bone pathology;
   d) optionally removing the therapeutic agent from the patient after a predetermined exposure time has elapsed;
   e) removing the therapy delivery apparatus from the bone cannula and optionally obstructing the cannula with an operative instrument or apparatus capable of being cooperatively and threadably received into the cannula for the purpose of obstructing it until a subsequent treatment session is initiated while leaving the bone cannula positioned in the patient, wherein the outer dermis undergoes wound closure;
   f) initiating a subsequent treatment session by re-accessing the cannular lumen and removing any instrument that may have been inserted into the bone cannula to temporarily block the same; and
   g) re-inserting the therapy delivery apparatus into the bone cannula in order to initiate the delivery of a second intended dose of the therapeutic agent.

2. The method of claim 1, wherein the therapeutic agent is a radiation source and the bone pathology is a tumor.

3. The method of claim 2, wherein the radiation source is a discrete radiation emitting particulate and the therapy delivery apparatus is a catheter.

4. The method of claim 3, wherein the particulate is selected from the group consisting of seeds, beads, or granules.

5. The method of claim 2, wherein the radiation source is a discrete radiation emitting particulate and the therapy delivery apparatus is a trocar.

6. The method of claim 1, wherein the therapeutic agent is a chemotherapeutic and the bone pathology is a tumor.

* * * * *